United States Patent [19]

Mayer et al.

[11] Patent Number: 5,863,922

[45] Date of Patent: Jan. 26, 1999

[54] PAIN-ALLEVIATING DRUG COMPOSITION AND METHOD FOR ALLEVIATING PAIN

[75] Inventors: David J. Mayer, Richmond; Donald D. Price, Richmond; Jianren Mao, Richmond, all of Va.; John W. Lyle, Belmar, N.J.

[73] Assignee: Virginia Commonwealth University, Richmond, Va.

[21] Appl. No.: 889,041

[22] Filed: Jul. 7, 1997

Related U.S. Application Data

[62] Division of Ser. No. 510,546, Aug. 2, 1995.

[51] Int. Cl.$^6$ ............... A61K 31/505; A61K 31/445; A61K 31/165

[52] U.S. Cl. ............... 514/270; 514/289; 514/629

[58] Field of Search ............... 514/270, 289, 514/629

[56] References Cited

U.S. PATENT DOCUMENTS 5,336,691  8/1994  Raffa et al. ............... 514/269

OTHER PUBLICATIONS

Dahl, J., Current Opinion in Anaesthesiology, 8:323–330 1995.

*Primary Examiner*—Phyllis G. Spivack
*Attorney, Agent, or Firm*—Dilworth & Barrese

[57] ABSTRACT

The analgesic effectiveness of a combination drug containing at least one analgesic is significantly enhanced by the addition of a nontoxic N-methyl-D-aspartate (NMDA) receptor antagonist thereto.

2 Claims, 1 Drawing Sheet

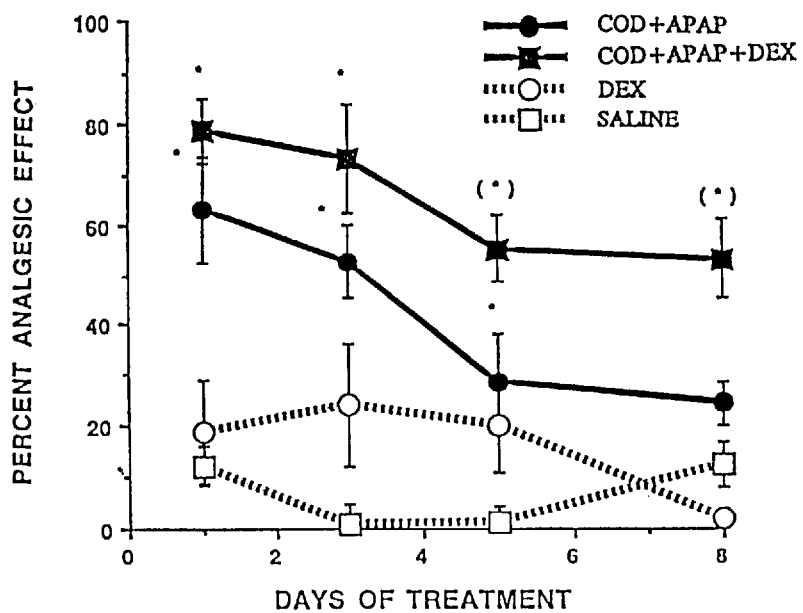
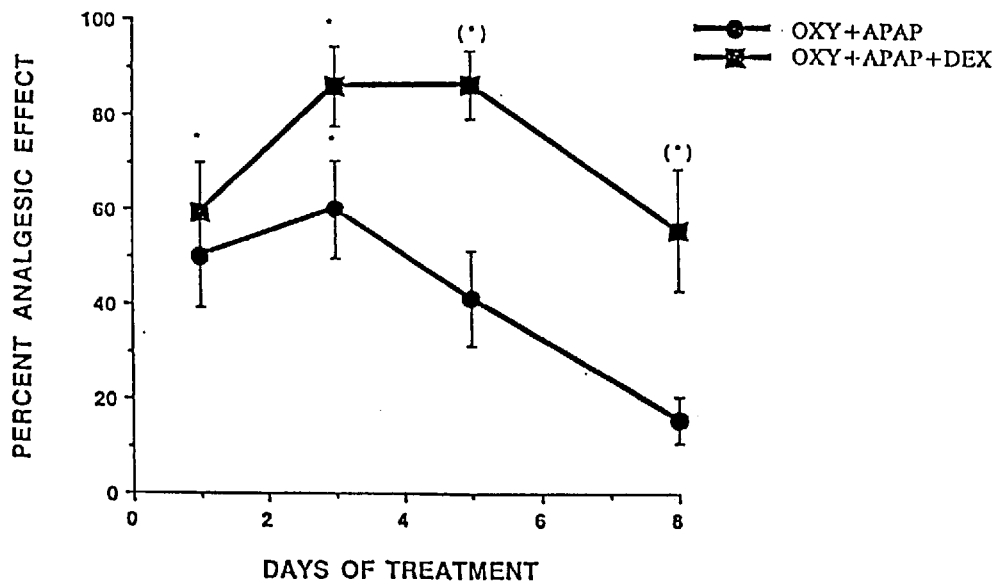

PAIN-ALLEVIATING DRUG COMPOSITION AND METHOD FOR ALLEVIATING PAIN

This is a divisional of copending application Ser. No. 08/510,546 filed Aug. 2, 1995, allowed.

BACKGROUND OF THE INVENTION

This invention relates to a pain-alleviating drug composition and method for alleviating pain. The drug composition includes as a first component a first analgesic which may be of the opioid type, e.g., codeine, dihydrocodeine, oxycodone, hydrocodone, meperidine, propoxyphene, pentazocine, etc., or of the nonopioid type, e.g., a coal tar analgesic such as acetaminophen or a nonsteroidal antiinflammatory drug (NSAID) such as aspirin or ibuprofen, as a second component, a sedative, e.g., of the barbiturate type such as butalbital or of the nonbarbiturate type such as diphenhydramine, dichloralphenazone, droperidol or promethazine, a skeletal muscle relaxant such as methocarbamol or carisoprodol and, where the first analgesic is of the opioid type, a second analgesic of the nonopioid type, e.g., acetaminophen, aspirin or ibuprofen, and as a third component, a nontoxic N-methyl-D-aspartate (NMDA) receptor antagonist such as dextrorphan or dextromethorphan.

A number of drug combinations for alleviating pain or treating other conditions associated with a pain component are known including the following: codeine phosphate and acetaminophen; hydrocodone bitartrate and acetaminophen; codeine phosphate and aspirin; hydrocodone bitartrate, acetaminophen, caffeine, chlorpheniramine maleate and phenylephrine hydrochloride; hydrocodone bitartrate and aspirin; dihydrocodeine bitartrate, acetaminophen and caffeine; dihydrocodeine bitartrate, aspirin and caffeine; codeine phosphate and promethazine hydrochloride; meperidine hydrochloride and promethazine hydrochloride; oxycodone hydrochloride and acetaminophen; oxycodone hydrochloride, oxycodone terephthalate and aspirin; pentazocine hydrochloride and acetaminophen; pentazocine hydrochloride and aspirin; propoxyphene napsylate and acetaminophen; propoxyphene hydrochloride and acetaminophen; propoxyphene hydrochloride, aspirin and caffeine; acetaminophen and diphenhydramine citrate; acetaminophen and diphenhydramine hydrochloride; acetaminophen, dichloralphenazone and isometheptene mucate; aspirin and butalbital; acetaminophen, butalbital and caffeine; aspirin, butalbital and caffeine; codeine phosphate, aspirin, butalbital and caffeine; aspirin and methocarbamol; aspirin and carisoprodol; codeine phosphate, aspirin and carisoprodol; and, fentanyl citrate and droperidol.

The analgesic component(s) of each of these combination drugs can cause adverse reactions. Opioid analgesics such as codeine, dihydrocodeine, oxycodone, hydrocodone, meperidine, propoxphene and pentazocine can produce tolerance and/or dependence. As for the nonopioid analgesics, acetaminophen has been known to cause fatal hepatic damage and the NSAIDs have a tendency to cause gastrointestinal side effects ranging from the relatively mild to the guite severe (ulceration of the stomach or duodenum). The risk of these adverse reactions is all the greater where their long term administration is concerned.

Dextromethorphan is the d-isomer of the codeine analog of levorphanol. Unlike the l-isomer, dextromethorphan is said to have no analgesic or addictive properties (Goodman and Gilman's, "The Pharmacological Basis of Therapeutics", 8th ed., McGraw-Hill, Inc. (1990), p. 518). The antitussive activity of dextromethorphan has led to its use in a variety of over-the-counter orally administered therapeutic compositions (tablets, syrups) for the relief of cold, influenza and/or cough conditions. Many, if not most, of these therapeutics also contain a nonopioid analgesic such as an NSAID.

U.S. Pat. No. 4,446,140 describes a method of treating mouth pain, i.e., pain or discomfort associated with the oral cavity, the teeth, gums and other mucosal surfaces of the lips, tongue and mouth resulting from such causes as toothache, denture irritations, canker sores, irritation related to inflamed gums, orthodontic tooth manipulation and appliances, oral surgery, etc., by administration of dextromethorphan alone or together with a conventional analgesic such as acetaminophen, indomethacin, ibuprofen or naproxen or a conventional anesthetic such as benzocaine or butacaine.

U.S. Pat. No. 5,321,012 discloses that administration of a nontoxic NMDA receptor antagonist such as dextrorphan or dextromethorphan prior to, with or following administration of an opioid analgesic such as morphine, codeine, and the like, inhibits the development of addiction to and/or dependence on the analgesic.

European Patent Application 0 081 823 describes a method of temporarily reducing pain and discomfort associated with dysmenorrhea by administration of dextromethorphan alone or in combination with one or more additional drugs, e.g., an analgesic such as acetaminophen, indomethacin, ibuprofen or naproxen.

SUMMARY OF THE INVENTION

It has now been found that the analgesic effectiveness of known combination drugs containing at least one analgesic component can be significantly enhanced by the addition of a nontoxic N-methyl-D-aspartate receptor antagonist thereto. In accordance with this invention, a pain-alleviating drug composition is provided which comprises:

a) a pharmacologically effective amount of a first component which is a first analgesic selected from the group consisting of opioid analgesic and nonopioid analgesic;

b) a pharmacologically effective amount of a second component which is selected from the group consisting of sedative, skeletal muscle relaxant and, where the first analgesic is of the opioid type, a second analgesic of the nonopioid type; and, c) an analgesia-enhancing amount of a third component which is a nontoxic N-methyl-D-aspartate receptor antagonist.

The foregoing pain-alleviating drug composition is useful for treating a variety of chronic pain and acute pain states, e.g., arthritic pain, lumbosacral pain, musculoskeletal pain, post-operative pain and headache. When, in accordance with the method of the invention, e.g., a surgical procedure, the drug composition herein is administered to a mammal that is either experiencing pain, e.g., of the aforementioned kind, or is about to be subjected to a pain-causing event, e.g., a surgical procedure, the resulting level of pain relief is significantly enhanced relative to that obtained with the same drug composition but one lacking the nontoxic N-methyl-D-aspartate (NMDA) receptor antagonist component. This ability of the NMDA receptor antagonist component to enhance the efficacy of the analgesic component(s) of the drug composition permits either a reduction in the amount of analgesic(s) in a dosage unit without a reduction in the level of pain relief or an increase in the level of pain relief without an increase in the amount of analgesic(s) in a dosage unit. Either capability offers essentially the same advantage, i.e., less analgesic is required for effective pain management. Given the adverse effects of the opioid and nonopioid analgesics noted above, such advantage is of considerable benefit to those requiring pain relief, particularly in relatively long term (e.g., 1–4 weeks) or chronic pain situations.

The expression "analgesia-enhancing" refers to any significant improvement in analgesic effectiveness of an analgesic or combination of analgesics expressed in terms of the level of analgesia and/or its duration.

The expression "N-methyl-D-aspartate receptor" shall be understood to include all of the binding site subcategories associated with the NMDA receptor, e.g., the glycine-binding site, the phenylcyclidine (PCP)-binding site, etc., as well as the NMDA channel. Thus, the invention herein contemplates the use of nontoxic substances that block an NMDA receptor binding site, e.g., dextrorphan or dextromethorphan, or that block the NMDA channel, e.g., a substance that blocks the magnesium or calcium channel.

The term "nontoxic" as used herein shall be understood in a relative sense and is intended to designate any substance that has been approved by the United States Food and Drug Administration ("FDA") for administration to humans or, in keeping with established regulatory criteria and practice, is susceptible to approval by the FDA for administration to humans. The term "nontoxic" is also used herein to distinguish the NMDA receptor antagonists, or blockers, that are useful in the practice of the present invention from NMDA receptor antagonists such as MK 801 (the compound 5-methyl-10,11-dihydro-5H-dibenze[a,d] cyclohepten-5,10-imine), CPP (the compound 3-[2-carboxypiperazin-4-yl] propyl-1-phosphonic acid) and PCP (the compound 1-(1-phenylcyclohexyl)piperidine) whose toxicities effectively preclude their therapeutic use.

The term "pain-alleviating" shall be understood herein to include the expressions "pain-suppressing" and "pain-inhibiting" as the invention is applicable to the alleviation of existing pain as well as the suppression or inhibition of pain which would otherwise ensue from an imminent pain-causing event.

The expression "combination drug" shall be understood herein to include any drug composition containing at least two therapeutically active components of which at least one is an opioid or nonopioid analgesic drug.

BRIEF DESCRIPTION OF THE DRAWINGS

In the accompanying drawings, FIGS. 1 and 2 are graphical presentations of experimental data comparing the analgesic effectiveness of known combination drugs with the same drugs additionally containing dextromethorphan hydrobromide in accordance with the invention and with dextromethorphan hydrobromide administered by itself.

DESCRIPTION OF THE PREFERRED
EMBODIMENTS

The first component of the drug composition of this invention is a first analgesic which can be of the opioid or nonopioid type. Useful opioid analgesics include morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine, pentazocine and their pharmaceutically acceptable salts. Useful nonopioid analgesics include the coal-tar analgesics, in particular, acetaminophen, and nonsteroidal antiinflammatory drugs (NSAIDs) such as aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, nabumetone, naproxen, oxaprozin, phenylbutazone, piroxicam, sulindac, tolmetin, zomepirac, their mixtures and their pharmaceutically acceptable salts.

The second component of the drug composition of this invention can be a sedative (a term used herein to refer to drugs that include not only the sedatives or sedative-hypnotics as such but all other drugs having a sedative action), a skeletal muscle relaxant, a second analgesic which is of the nonopioid type when the first analgesic is of the opioid type or combinations of any of the foregoing. The sedatives include the barbiturate sedatives such as amobarbital, aprobarbital, butabarbital, butabital, mephobarbital, metharbital, methohexital, pentobarbital, phenobartital, secobarbital, talbutal, theamylal, thiopental and their pharmaceutically acceptable salts and the nonbarbiturate sedatives include benzodiazepines having a sedative action such as chlordiazepoxide, clorazepate, diazepam, flurazepam, lorazepam, oxazepam, temazepam, triazolam and their pharmaceutically acceptable salts, $H_1$ antagonists having a sedative action such as diphenhydramine, pyrilamine, promethazine, chlorpheniramine, chlorcyclizine and their pharmaceutically acceptable salts, neuroleptics such as droperidol and miscellaneous sedatives such as glutethimide, meprobamate, methaqualone, dichloralphenazone and their pharmaceutically acceptable salts. Skeletal muscle relaxants include baclofen, carisoprodol, chlorzoxazone, cyclobenzaprine, methocarbamol, orphrenadine and their pharmaceutically acceptable salts.

The third component of the drug composition of this invention is a nontoxic NMDA receptor antagonist. Among the nontoxic substances that block the NMDA receptor and as such are useful for enhancing the analgesic activity of the combination therapeutic in accordance with this invention are dextromethorphan ((+)-3-hydroxy-N-methylmorphinan) and its metabolite dextrorphan ((+)-3-hydroxy-N-methylmorphinan), their mixtures and their pharmaceutically acceptable salts. Other useful nontoxic substances that block the NMDA receptor include ketamine, memantine, pyrroloquinoline quinone and cis-4-(phosphonomethyl)-2-piperidinecarboxylic acid. Of the NMDA receptor antagonists, dextromethorphan is preferred for use herein due to its high degree of proven safety and its ready availability (as the hydrobromide salt). While dextrorphan and its pharmaceutically acceptable salts will also provide excellent results, it is not known to be in commercial manufacture at this time.

The amounts of first and second component present in a unit dose of the drug composition of this invention can be the same as those employed in comparable dosage forms of known combination drugs such as those previously mentioned. The amount of third component, i.e., the nontoxic NMDA receptor antagonist, will be at least that which is required to significantly enhance the analgesic effectiveness of the analgesic(s) present in the dose. Suitable amounts of NMDA receptor antagonist for a given composition and dosage form can be readily determined employing routine procedures. In general, amounts of NMDA receptor antagonist that will significantly enhance the analgesic effectiveness of the therapeutic composition herein can vary from about 10 to about 100, and preferably from about 15 to about 60, mg per unit dose.

All modes of administrations are contemplated for the drug composition of this invention, e.g., administration can be orally, rectally or by intravenous, intramuscular, subcutaneous, intrathecal, epidural or intracerebroventricular injection. The drug composition will ordinarily be formulated with one or more pharmaceutically acceptable ingredients in accordance with known and established practice. Thus, the composition can be formulated as a liquid, powder, elixir, injectable solution or suspension, etc. Formulations for oral use can be provided as tablets, caplets or hard capsules wherein the pharmacologically active ingredients are mixed with an inert solid diluent such as calcium carbonate, calcium phosphate or kaolin, or as soft gelatin capsules wherein the active ingredients are mixed with an oleaginous medium, e.g., liquid paraffin or olive oil.

Aqueous suspensions can include pharmaceutically acceptable excipients such as suspending agents, e.g., sodium carboxymethyl cellulose, methylcellulose, hydroxypropylmethylcellulose, sodium alginate, polyvinylpyrrolidone, gum tragacanth and gum acacia; dispersing or wetting agents such as naturally occurring phosphatide, e.g., lecithin, or condensation products of an alkylene oxide with fatty acids, e.g., polyoxyethylene stearate, or condensation products of ethylene oxide with long chain aliphatic alcohols, e.g, heptadecaethyleneoxycetanol, or condensation products of ethylene exide with partial esters derived from fatty acids and a hexitol, e.g., polyoxyethylene sorbitol monoleate or condensation products of ethylene oxide with partial esters derived from fatty acids and hexitol anhydrides, e.g., polyoxyethylene sorbitan monooleate. The aqueous suspensions can also contain one or more preservatives, e.g., ethyl-or-n-propyl-p-hydroxy benzoate, one or more coloring agents, one or more flavoring agents and one or more sweetening agents, such as sucrose, saccharin or sodium or calcium cyclamate.

In addition to the components already cited, the drug composition herein can contain one or more other pharmacologically active components, e.g., caffeine (a stimulant), chlorpheniramine maleate (an antihistamine), phenylephrine hydrochloride and phenylpropanolamine hydrochloride (decongestants) and isometheptene mucate (a sympathomimetic).

EXAMPLES 1–26

The following unit dosage forms are illustrative of the pain-alleviating therapeutic composition of this invention:

| Example | Dosage Form | First Component (mg) | Second Component (mg) | Third Component (mg) | Additional Active Component(s) (mg) |
|---|---|---|---|---|---|
| 1 | tablet | codeine phosphate (30) | acetaminophen (650) | dextromethorphan hydrobromide (30) | |
| 2 | tablet | hydrocodone bitartrate (5) | acetaminophen (500) | dextromethorphan hydrobroimide (30) | |
| 3 | tablet | codeine phosphate (30) | aspirin (325) | dextromethorphan hydrobromide (30) | |
| 4 | tablet | hydrocodone bitartrate C5) | acetaminophen (250) | dextromethorphan hydrobromide (30) | caffeine (30); chlorpheniramine maleate (2); phenylphrine hydrochloride (10) |
| 5 | tablet | hydrocodone bitartrate (5) | aspirin (500) | dextromethorphan hydrobromide (30) | |
| 6 | capsule | dihydrocodeine bitartrate (16) | acetaminophen (356) | dextromethorphan (30) | caffeine (30) |
| 7 | tablet | dihydrocodeine bitartrate (16) | aspirin (356) | dextromethorphan hydrobromide (30) | caffeine (30) |
| 8 | syrup | codeine phosphate (10) | promethazine hydrochloride (6.25) | dextromethorphan hydrobromide (30) | |
| 9 | injectable | meperidine hydrochloride (25 per ml) | promethazine hydrochloride (25 per ml) | dextromethorphan hydrobromide (10 per ml) | |
| 10 | capsules | oxycodone hydrochloride (5) | acetaminophen (500) | dextromethorphan hydrobromide (30) | |
| 11 | tablet | oxycodone hydrochloride (4.5); oxycodone terephthlate (0.38) | aspirin (325) | dextromethorphan hydrobromide (30) | |
| 12 | caplet | pentazocine hydrochloride (12.5) | aspirin (325) | dextromethorphan hydrobromide (30) | |
| 13 | tablet | pentazocine hydrochloride (12.5) | aspirin (325) | dextromethorphan hydrobromide (30) | |
| 14 | tablet | propoxyphene napsylate (100) | acetaminophen (650) | dextromethorphan hydrobromide (30) | |
| 15 | capsule | propoxyphene hydrochloride (65) | aspirin (389) | dextromethorphan hydrobromide (30) | caffeine (32) |
| 16 | caplet | acetaminophen (500) | diphenhydramine citrate (38) | dextromethorphan hydrobromide (30) | |

-continued

| Example | Dosage Form | First Component (mg) | Second Component (mg) | Third Component (mg) | Additional Active Component(s) (mg) |
|---|---|---|---|---|---|
| 17 | tablet | acetaminophen (500) | diphenhydramine hydrochloride (25) | dextromethorphan hydrobromide (30) | |
| 18 | capsule | acetaminophen (325) | dichloralphen-azone (100) | dextromethorphan hydrobromide (30) | isomet heptene mucate (65) |
| 19 | tablet | aspirin (650) | butalbital (50) | dextromethorphan hydrobromide (30) | |
| 20 | tablet | acetaminophen (325) | butalbital (50) | dextromethorphan hydrobromide (30) | caffeine (40) (40) |
| 21 | capsule | aspirin (325) | butalbital (50) | dextromethorphan hydrobromide (30) | caffeine (40) |
| 23 | tablet | aspirin (325) | methocarbamol (400) | dextromethorphan hydrobromide (30) | |
| 24 | tablet | aspirin (325) | carisprodol (200) | dextromethorphan hydrobromide (30) | |
| 25 | tablet | codeine phosphate (16) | aspirin (325); carisprodol (200) | dextromethorphan hydrobromide ( 30 | |
| 26 | injectable | fentanyl citrate (50 µg) (as base) per ml) | droperidol (2.5 per ml) | dextromethorphan hydrobromide (15 per ml) | |

In each of these unit doses, the NMDA receptor antagonist dextromethorphan hydrobromide significantly enhances the analgesic activity of the analgesic component(s).

EXAMPLE 27

This example demonstrates the enhanced analgesic effects resulting from the addition of dextromethorphan hydrobromide (DEX) to a drug combination of known type, specifically, one containing as active ingredients codeine hydrochloride (COD) and acetaminophen (APAP).

Each test dosage was administered intragastrically to one of four groups (n=10) of test animals, adult male Sprague-Dawley rats each weighing from 350–400 g. The analgesia produced by each drug was measured by the tail-flick test of Trujillo et al., *Science*, 251:85–87 (1991). Tail-flick latencies were tested at one and one half hours after oral administration on Day 1, Day 3, Day 5 and Day 8. Differences in post-administration tail-flick latencies across groups on a given test day were examined using a one-way analysis of variance (ANOVA) followed by post-hoc Waller-Duncan k-ratio t (WD) tests.

One of the following four dosages was administered twice a day to one of the test groups (all dosage amounts in mg/kg body weight): COD(30)+APAP(300), COD(30)+APAP(300)+DEX(50), DEX(50) and saline (control). The observed tail-flick latencies provided a measurement of the analgesic effect for each dosage over the eight day test period. As shown in FIG. 1 and as expected, the DEX(50) and saline (control) dosages were essentially ineffectual as analgesics. The COD(30)+APAP(300) dosage provided an initial response of moderate analgesia but declined significantly thereafter to the point that on Day 8, the dosage provided little effective analgesia. However, in the case of the COD(30)+APAP(300)+DEX(50) dosage, initial analgesic response was significantly higher than that of the COD(30)+APAP(300) dosage and while falling off, continued to provide a significant level of pain relief through Day 8.

EXAMPLE 28

Employing test procedures similar to those described in Example 27, this example shows the enhanced analgesic effects resulting from the addition of DEX to another drug combination of known type, this one containing oxycodone (OXY) and APAP as its active ingredients.

One of the following two dosages was administered twice a day to one of two groups (n=10) of Sprague-Dawley rats: OXY(9)+APAP(585) and OXY(9)+APAP(585)+DEX(50). As shown in FIG. 2, the OXY(9)+APAP(585) dosage provided an initial level of moderate pain relief and a slight increase therein over the next two days. From Day 3 on, analgesic effectiveness declined sharply and at Day 8, was negligible. In sharp contrast to this dose-response profile, the OXY(9)+APAP(585)+DEX(50) dosage provided a similar level of initial analgesia but one which increased sharply through Day 3, remained at a high level through Day 5 and though declining thereafter, continued to provide a significant level of pain relief at Day 8.

What is claimed is:

1. A drug composition comprising:
   a) a pharmacologically effective amount of a first component which is the analgesic acetaminophen;
   b) a pharmacologically effective amount of a second component which is the sedative butalbital; and,
   c) an analgesia-enhancing amount of a third component which is a nontoxic N-methyl-D-aspartate receptor antagonist selected from the group consisting of dextrorphan, dextromethorphan, their mixtures and their pharmaceutically acceptable salts.

2. A method for alleviating pain which comprises administering to a mammal which is either experiencing pain or is about to be subjected to a pain-causing event a pain-alleviating amount of a drug composition comprising:
   a) a pharmacologically effective amount of a first component which is the analgesic acetaminophen;
   b) a pharmacologically effective amount of a second component which is the sedative butalbital; and,
   c) an analgesia-enhancing amount of a third component which is a nontoxic N-methyl-D-aspartate receptor antagonist selected from the group consisting of dextrorphan, dextromethorphan and their pharmaceutically acceptable salts.

* * * * *